United States Patent [19]
Beckwith

[11] 3,947,416
[45] Mar. 30, 1976

[54] AZAISATOIC ANHYDRIDES
[75] Inventor: Athelstan L. J. Beckwith, Adelaide, Australia
[73] Assignee: The Sherwin-Williams Company, Cleveland, Ohio
[22] Filed: Feb. 10, 1975
[21] Appl. No.: 548,443

Related U.S. Application Data
[62] Division of Ser. No. 878,552, Nov. 20, 1969, Pat. No. 3,887,550.

[52] U.S. Cl. .............................................. 260/244 R
[51] Int. Cl.$^2$ ....................................... C07D 498/04
[58] Field of Search ..................... 260/244 R, 244 A

[56] References Cited
UNITED STATES PATENTS
3,622,573   11/1971   Schlaudecker .................. 260/244 A Primary Examiner—Natalie Trousof
Attorney, Agent, or Firm—John C. Purdue; James D. McNeil

[57] ABSTRACT

A method for producing heterocyclic acid anhydrides and pyrimidinediones from the corresponding acids, dicarboxamides, 2,3-and 3,4-pyridinedicarboxamides, and N-monosubstituted 2,3-and 3,4-pyridinedicarboxamides, in which the aforesaid compounds are reacted with lead tetra-acetate in the presence of a suitable anhydrous inert solvent.

2 Claims, No Drawings

AZAISATOIC ANHYDRIDES

This is a division, of application Ser. No. 878,552 filed Nov. 20, 1969 now U.S. PAT. No. 3,887,550.

BACKGROUND OF THE INVENTION

1. Field of the Invention

In recent years considerable interest in isatoic anhydride has developed because of the facility with which it and its ring substituted analogues can be used as intermediates in the production of pharmaceuticals*, agricultural chemicals**, and anthranilic acid esters which are used as perfume essences and flavoring materials. Such interest has stimulated a search for new, less expensive and non-hazardous methods of production of isatoic anhydride and its substituted analogues.

* U.S. Pat. No. 3,170,955 (1965)
  U.S. Pat. No. 3,162,684 (1964)
  U.S. Pat. No. 3,163,646 (1964)
  U.S. Pat. No. 3,120,523 (1964)
  Neth. Apl. 6,407,857 (1965)
  U.S. Pat. No. 3,252,986 (1966)
  U.S. Pat. No. 3,274,194 (1966)

** British 894,435 (1962)
   British 865,735 (1961)
   U.S. Pat. No. 3,244,503 (1966)
   Germany 1,210,242 (1966)

Many of the pyrimidinediones and ring substituted analogues formed by the method of the invention are useful as agricultural chemicals, in particular as herbicides. Specifically, many of the compounds have been found to have utility as plant growth regulators, total herbicides, selective weed killers, and defoliating agents.

In recent years increased crop yields have been made possible by the development and use of chemicals which are specifically toxic to weeds, yet do not damage crops around which they are applied. In general, the currently available chemicals which are most desired for their selectivity and as total herbicides are sufficiently expensive that cost is a significant factor in their use. Therefore, new compounds and inexpensive methods for producing such compounds are constantly being sought. The use of 3-substituted pyrimidinediones is disclosed in application Ser. No. 740,090 filed June 26, 1968, now abandoned.

In addition, while many compounds presently on the market are effective against certain species of weeds, they are ineffective against others, or against certain strains or weeds. Apparently, resistant strains develop by a phenomenon which can be likened to "natural selection". Thus new herbicides which have broad spectrum effectiveness against a wide variety of weeds are continually being sought.

It is an object of the present invention to provide an improved method for producing heterocyclic acid anhydrides and pyrimidinediones.

It is a further object to provide a method for the production of heterocyclic acid anhydrides and pyrimidinediones which is non-hazardous and simple, and which does not require exotic or expensive starting materials or complicated apparatus.

It is a further object of the invention to provide an easy one-step method for the production of compounds having the following formulas:

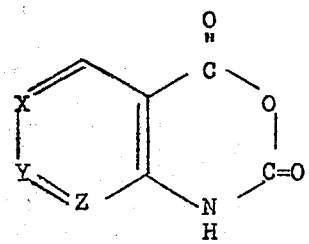

Heterocyclic acid anhydride

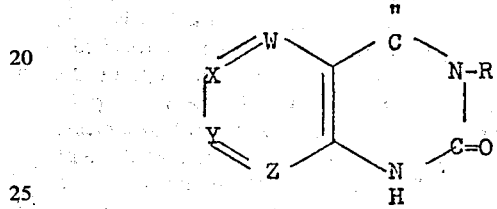

Heterocyclic pyrimidinedione wherein each of W, X, Y and Z is N or CH and, in the acid anhydride, not more than one of X, y and Z is N, while, in the pyrimidinediones, not more than two of W, X, Y and Z can be N, and R is hydrogen or an alkyl group having not more than 8 carbon atoms.*

* Alkyl group is used in the ordinary sense of the word to indicate a straight-chain alkyl group.

BRIEF SUMMARY OF THE INVENTION

The method of the instant invention comprises reaction in an inert anhydrous solvent (1) substantially equivalent amounts of lead tetra-acetate with (2) a compound having the formula

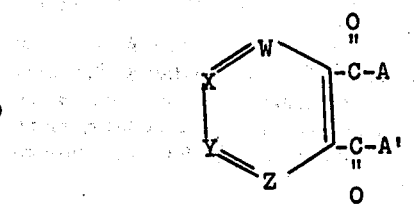

wherein each of A and A' is OH or NHR and W, X, Y, Z and R have the meanings set forth above, with the proviso that not more than one of A and A' is OH and when either of A and A' is OH, R is hydrogen, W is CH and not more than one of X, Y and Z is N, agitating the reaction mixture at a temperature sufficiently high that reaction occurs and recovering the acid anhydride or pyrimidinedione.

PREPARATION OF STARTING MATERIALS

Compounds represented by the foregoing formula, when either A and A' is OH, are phthalamic acid and ringsubstituted nitrogen analogues, named as carbamylnicotinic acids, which constitute the starting materials for the preparation of the acid anhydrides, they can be prepared as described in the references cited in Examples I through VI.

Pyridine-2,3- and 3,4-dicarboxamides and N-monosubstituted 2,3- and 3,4-pyridinedicarboxamides which constitute the starting materials for the preparation of pyrimidinediones, can be made from corresponding dicarboxylic acids according to the method outlined below, through the imide, which is then reacted with NH₃ or a suitable amine. The preparation of N²-n-butyl-2,3-pyridinedicarboxamide is used as an example.

EXAMPLE A

A 2-liter, 3-necked flask equipped with a stirrer and a thermometer, and partially immersed in an oil bath was charged with 400 g. of 2,3-pyridinedicarboxylic acid, 400 g. acetamide and 400 ml. acetic anhydride. Agitation was begun and continued throughout the reaction. The reaction mixture was then heated rapidly to a temperature of 136°* and held at that temperature for 2 hours. During this period the acetic acid which was produced was distilled off. At the end of this time, the mixture was cooled, the solids removed by filtration, and the filtrate set aside. The solids were washed with cold methanol, dried, and weighed. The yield was 251.6 g. light tan material having a melting point of 239°–240°. The filtrate, which had been set aside, was reduced in volume and a further yield of 9.2 g. of imide having a melting point of 239°–240° obtained. The total yield was 260.8 g. 2,3-pyridinedicarboximide. The 2,3-pyridinedicarboximide was used to prepare N²-n-butyl-2,3-pyridinedicarboxamide in the following manner.

* All temperatures reported herein and in the attached claims are in degrees Centigrade. A 500 ml. flask equipped with a stirrer, condenser, thermometer, bubbler, and addition funnel, and partially immersed in an ice bath, was charged with 16.5 g. pyridinedicarboximide and 100 ml. benzene. Agitation of the flask contents was begun and continued throughout the duration of the reaction. An addition of 11.0 g. n-butylamine was then commenced and charged over a 2 minute period. After the charging, the reaction mixture was stirred for an additional two hours and 30 minutes, during which time the temperature of the reaction mixture reached a high of 45°. At the end of this time, the thick slurry which had formed was cooled to about 10°, the solids were removed by filtration, and the filtrate was set aside. The solids were then washed with cold benzene and dried. The yield was 21.4 g. product which had a melting point of 87°–95°, and was identified by infrared spectroscopy as a mixture consisting predominately of N²-n-butyl-2,3-pyridinedicarboxamide with a small amount of N³-n-butyl-2,3-pyridinedicarboxamide.

The unsubstituted 2,3- and 3,4-dicarboxamides of pyridine and the other N-monosubstituted 2,3- and 3,4-dicarboxamides of pyridine can be produced in the same manner by reaction of the corresponding imide with the appropriate amine or NH₃. The reaction can be illustrated as follows:

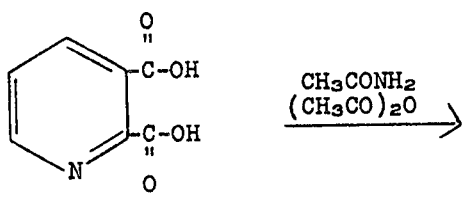

2,3-pyridinedicarboxylic acid

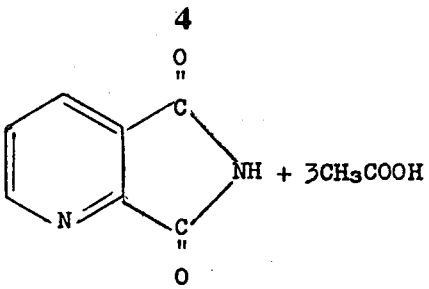

2,3-pyridinedicarboximide

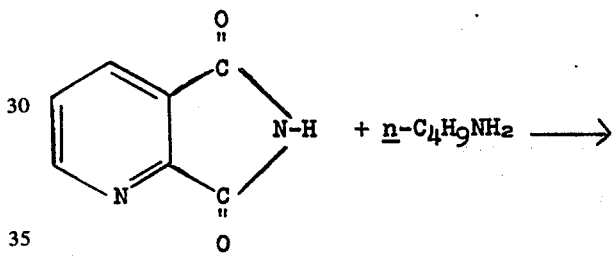

2,3-pyridinedicarboximide

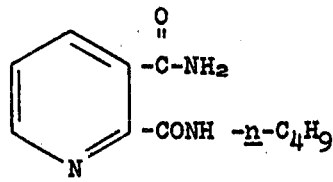

N²-n-butyl-2,3-pyridinedicarboxamide

This invention can be more clearly understood by reference to the following examples.

EXAMPLE I

Preparation of Isatoic Anhydride

A 250 ml. flask was charged with 2.0 g. phthalamic acid* suspended in 100 ml. dry benzene, and heated to boiling. A 5.4 g. portion of lead tetra-acetate was added to the boiling suspension, and the reaction mixture was heated under reflux, with stirring, for 48 hours. The reaction mixture was then cooled and solids were separated therefrom by filtration. The residue was washed 2 times with water; isatoic anhydride was recrystallized from dioxane, and dried in vacuo for 2 hours. The final yield of isatoic anhydride amounted to 0.87 g. tan solids, melting point 243°, and represented 44 percent of theory based on the phthalamic acid. The structure was confirmed by infrared spectroscopy.

* E. Chapman and H. Stephen, J. Chem. Soc., 1925, 127, 1791

EXAMPLE II

Preparation of Isatoic Anhydride

A 100 ml. flask was charged with 2.0 g. phthalamic acid suspended in 20 ml. dimethylformamide at room temperature. A 5.4 g. portion of lead tetra-acetate was added to the suspension, and the reaction mixture was held at room temperature for 40 minutes. The reaction mixture was poured into 30 ml. water. Isatoic anhydride was filtered from the water, recrystallized from dioxane, and dried in vacuo for 2 hours. The final yield of isatoic anhydride amounted to 1.07 g. tan solids, melting point 243°, and represented 54 percent of theory based on the phthalamic acid.

EXAMPLE III

Preparation of 3-Azaisatoic Anhydride

A 100 ml. flask was charged with 2.0 g. 2-carbamylnicotinic acid* suspended in 20 ml. dimethylformamide. A 5.5 g. portion of lead tetra-acetate was added to the suspension, and the mixture was stirred at 50°–60° for 1 hour. The reaction mixture was poured into 20 ml. water; solids were separated by filtration, and 3-azaisatoic anhydride was recrystallized from dioxane, and dried in vacuo for 2 hours. The final yield of 3-azaisatoic anhydride amounted to 1.48 g., melting point 217°–219°, and represented 75 percent of theory. The structure was confirmed by elemental analysis and infrared spectroscopy.

* F. G. Mann and J. A. Reid, J. Chem. Soc., 1952, 2057.

EXAMPLE IV

Preparation of 4-Azaisatoic Anhydride

A 50 ml. flask was charged with 0.94 g. 3-carbamylisonicotinic acid suspended in 8 ml. dimethylformamide. A 2.5 g. portion of lead tetra-acetate was added to the suspension, and the reaction mixture was stirred at 20° for 10 minutes. The reaction mixture was then warmed to 45° and stirred for 10 minutes. The cooled mixture was poured onto 30 grams crushed ice and the pale yellow solids were collected by filtration and dried in vacuo. Extensive decomposition of the product occurred upon attempted recrystallization from organic solvents. The final yield of 4-azaisatoic anhydride amounted to 0.65 g., melting point 218°, with decomposition, and represented 70 percent of theory. The structure was identified by elemental analysis, infrared spectroscopy and mass spectrometry.

EXAMPLE V

Preparation of 5-Azaisatoic Anhydride

A 50 ml. flask was charged with 2.6 g. lead tetra-acetate suspended in 10 ml. dimethylformamide and stirred while a solution of 0.96 g. of 4-carbamylnicotinic acid in 5 ml. dimethylformamide was added dropwise during 10 minutes. The mixture was stirred for 10 minutes after completion of the addition, then poured onto 40 g. crushed ice. A precipitate of cream solids was collected by filtration, washed with water and dried in vacuo. The yield of 5-azaisatoic anhydride amounted to 0.68 g., melting point 180° with decomposition, and represented 72 percent of theory. On attempted purification by crystallization from organic solvents, extensive decomposition occurred. The structure was confirmed by elemental analysis, infra-red spectroscopy and mass spectrometry.

EXAMPLE VI

Preparation of Pyrazino [2,3-d]Pyrimidine-2,4(1H,3H)-Dione

A 50 ml. flask was charged with 0.90 g. pyrazine-2,3-dicarboxamide dissolved in 16 ml. dimethylformamide. A 2.4 g. portion of lead tetra-acetate was added to the solution and the reaction mixture was stirred at 40° for 15 minutes. The reaction mixture was cooled, 30 g. of ice was added and after 1 hour the mixture was filtered. Crystallization of the residue from water gave, after drying in vacuo, a yield of 0.64 g. of pyrazino[2,3-d]pyrimidine-2,4(1H,3H)-dione, melting point 364°–365°, which represented 71 percent of theory. The structure was confirmed by infra-red spectroscopy.

EXAMPLE VII

Preparation of 2,4(1H,3H)-Quinazolinedione

A 50 ml. flask was charged with 1.0 g. phthalamide suspended in 10 ml. dimethylformamide. A 2.7 g. portion of lead tetra-acetate was added to the suspension, and the reaction mixture was stirred at 50°–60° for 1 hour. The reaction mixture was cooled, diluted with 15 ml. water, and filtered. Sublimation of the residue at 200° at an absolute pressure of 0.01 mm Hg gave a yield of 0.80 g. of 2,4(1H,3H)-quinazolinedione, melting point 351°–352°, and represented 81 percent of theory based on the phthalamide. The structure was confirmed by elemental analysis and infrared spectroscopy.

EXAMPLE VIII

Preparation of Pyrido[2,3-d]Pyrimidine 2,4(1H,3H)-Dione

A 50 ml. flask was charged with 0.9 g. pyridine-2,3-dicarboxamide suspended in 10 ml. dimethylformamide. A 2.4 g. portion of lead tetra-acetate was added to the suspension, and the reaction mixture was stirred at 50°–60° for 20 minutes and filtered. Sublimation of the residue at 200° at an absolute pressure of 0.01 mm. Hg gave a yield of 0.8 g. pyrido[2,3-d]pyrimidine-2,4(1H,3H)-dione, melting point 360°, and represented 90 percent of theory based on the pyridine-2,3-dicarboxamide. The structure was confirmed by infrared spectroscopy.

EXAMPLE IX

Preparation of Pyrido[3,4-d]Pyrimidine-2,4 (1H,3H)-Dione

A 50 ml. flask was charged with 1.0 g. pyridine-3,4-dicarboxamide suspended in 10 ml. dimethylformamide. A 2.4 g. portion of lead tetra-acetate was added to the suspension, the reaction mixture stirred at 50°–60° for 1 hour, cooled and filtered. Sublimation of the residue at 210°/0.01 mm. gave a yield of 1.0 g. of pyrido[3,4-d]pyrimidine-2,4(1H,3H)-dione, melting point 365°, representing 100 percent theory based on the pyridine-3,4-dicarboxamide. The structure was confirmed by elemental analysis and infrared spectroscopy.

EXAMPLE X

Preparation of 3-Methyl-2,4(1H,3H)-Quinazolinedione

A 50 ml. flask was charged with 1.0 g. N-methylphthalamide suspended in 11 ml. dimethylformamide. A 2.6 g. portion of lead tetra-acetate was added to the suspension, and the reaction mixture stirred at 40°–50° for 2 hours. The reaction mixture was diluted with 15 ml. water, cooled and filtered. The yield amounted to 0.89 g., melting point 230°–232°, representing 88 percent of theory based on the N-methylphthalamide. The structure was confirmed by infrared spectroscopy.

EXAMPLE XI

Preparation of 3-n-Butyl-Pyrido[3,2-d]Pyrimidine-2,4(1H,3H)-Dione

A 100 ml. flask was charged with 9.0 g. of a mixture of $N^2$-n-butyl-2,3-pyridine-dicarboxamide and $N^3$-n-butyl-2,3-pyridine-dicarboxamide suspended in 70 g. dimethylformamide. An 18.0 g. portion of lead tetra-acetate was added, and the reaction mixture stirred at 60° for 2 hours. The reaction mixture was poured into 200 ml. water. The precipitate was filtered from the water, recrystallized from dioxane, and dried at 100°, for about 1 hour. The final yield of 3-n-butyl-pyrido[3,2-d] and 3-n-butyl-pyrido[2,3-d]pyrimidine-2,4(1H,3H)-dione amounted to 8.4 g., melting point 200°–210°, and represented 93 percent of theory based on the dicarboxamide starting material. The structure was determined by nuclear magnetic resonance spectroscopy to consist of 78 percent of the [3,2-d]isomer and 22 percent of the [2,3-d]isomer.

EXAMPLE XII

Preparation of 3-Methyl Pyrazino[2,3-d]Pyrimidine-2,4(1H,3H)-Dione

A 50 ml. flask was charged with 0.90 g. N-methylpyrazine-2,3-dicarboxamide dissolved in 16 ml. dimethylformamide. A 2.4 g. portion of lead tetraacetate was added to the solution and the reaction mixture was stirred at 25° for 15 minutes. The reaction mixture was cooled, 30 g. of ice was added and after 1 hour the mixture was filtered. Crystallization of the residue from a mixture of water and dimethylformamide gave, after drying in vacuo, a yield of 0.76 g. of 3-methyl-pyrazine[2,3-d]pyrimidine-2,4(1H,3H)-dione, melting point 342°–343°, which represented 86 percent of theory. The structure was confirmed by elemental analysis, infra-red spectroscopy and mass spectrometry.

DISCUSSION OF THE REACTION MEDIUM

The improved method of the invention can be carried out in various inert, anhydrous solvents and combinations of such solvents. Although the reaction proceeds in a non-polar solvent such as benzene, as illustrated in Example II, dipolar aprotic solvents are the preferred reaction medium. The presence of a "dipole moment $(u)$" in such a dipolar aprotic solvent molecule contributes to the ease of solubility of the reacting compounds and to an improved reaction which takes place more readily than in a non-polar reaction medium. The reactions in dipolar aprotic solvents can be carried out at a lower temperature and will proceed at a much faster rate than reactions carried out in non-polar solvents. The preferred dipolar aprotic solvents of the method of the invention are: dimethylformamide, diethylformamide, dimethylacetamide, diethylacetamide, and dimethylsulfoxide. Aromatic solvents which are operable as reaction media are benzene, ethylbenzene, xylene, toluene, and pyridine. Combinations of dipolar solvents and combinations of dipolar and aromatic solvents are also operable as reaction media.

In addition to being useful as discussed above, acid anhydrides produced by the method of the invention are useful as intermediates for the production of pyrimidine diones which can be used as herbicides. For example, 3-azaisatoic anhydride can be dissolved in dimethylformamide and reacted with a substantially stoiciometric amount of isopropyl amine to produce 2-amino-N-isopropylnicotinamide. The reaction is conveniently conducted at a temperature of about 45°–50° until carbon dioxide evolution ceases. The 2-amino-N-isopropylnicotinamide can then be reacted with phosgene to produce 3-isopropyl pyrido[2,3-d]pyrimidine-2,4 (1H,3H)-dione. This reaction can be conducted under ambient pressure in p-dioxane as a solvent, preferably in the presence of triethylamine as an HCl absorber, at a temperature in the vicinity of 100°.

The 3-isopropyl pyrido[2,3-d]pyrimidine-2,4 (1H,3H)-dione for which 3-azaisatoic anhydride is an intermediate, as discussed above, can be used as a herbicide, dissolved in acetone, by spraying onto soil which has been prepared for planting. A light working of the soil after spray application is desirable, e.g., by dragging or disking to work the 3-isopropyl pyrido [2,3-d]pyrimidine-2,4(1H,3H)-dione into the soil. The soil can then be planted in a conventional manner. The 3-isopropyl pyrido[2,3-d]pyrimidine-2,4(1H,3H)-dione, applied at a rate of 16 pounds per acre, is innocuous to alfalfa, but shows herbicidal activity against volunteer corn, wild oats, cheat grass, foxtail, barnyard, crab grass, nut grass, Johnson grass, volunteer snap beans, soybeans, pig weed, lambsquarter and marigold and, at higher application rates, can be used as a total herbicide.

The 2-amino-N-isopropylnicotinamide for which 3-azaisotoic anhydride is an intermediate, as also discussed above, can also be dissolved in acetone and used as described in the preceding paragraph hereof at an application rate of 16 pounds per acre as a preemergence herbicide for the control of wild oats.

The 4-azaisatoic anhydride and the 5-azaisatoic anhydride, produced as described above according to the method of the invention, are believed to be new compounds, all attempts at their production by an aqueous Hoffman reaction which has been used to produce 3-azaisatoic anhydride having failed. The 4- and 5- azaisatoic anhydrides are also useful as chemical intermediates. They undergo reactions analogous to those discussed above with isopropyl and other amines to produce the isomeric N-substituted amides, from which the isomeric pyrimidine diones can likewise be produced by reaction with phosgene.

Some of the pyrimidine diones produced by the method of the invention are useful as herbicides. For example, 3-n-butyl pyrido[3,2-d]pyrimidine-2,4(1H,3H)-dione, applied as described above at a rate of 16 lbs. per acre, was found to provide 100 percent control of alfalfa, corn, wild oats, cheatgrass, foxtail, barnyardgrass, nutgrass, Johnsongrass, snapbeans, yellow rocket, chickweed, cucumber, pigweed and velvetleaf, 70 percent control of lambsquarters and 90 percent control of crabgrass.

The pyrimidine diones produced by the method of the invention which are not particularly useful as herbicides are unexpectedly useful because of their close similarity, from a structural chemical standpoint, to compounds having extremely high orders of activity. For example, 3-n-butyl pyrazino[2,3-d]pyrimidine-2,4(1H,3H)-dione was a considerably lower order of herbicidal activity than does 3-n-butyl pyrido[3,2-d]pyrimidine-2,4(1H,3H)-dione, and members of other families of pyrimidine diones produced by the method of the invention are substantially inert as herbicides. The close structural similarities among these several compounds, coupled with the fact reported herein of the significant difference in order of herbicidal activity provides the basis for an orderly investigation, on the basis of molecular models, of the relationship between chemical structure and herbicidal activity, the development of a theory explaining this relationship, and consequent significant advance in the useful arts on the basis of intelligent application of the theoretical explanation by skilled workers in the art.

The corrosion inhibiting characteristics of the pyrimidine diones produced by the method of the invention have been demonstrated by immersing carefully cleaned, dried and weighed 1010 steel coupons in 5 percent sulfuric acid to which a minor amount of the pyrimidine dione has been added for a period of 4 hours at 75° and then again carefully cleaning, washing, drying and weighing the coupons. The percentage weight loss, which is 100 times the weight loss in grams divided by the weight of the coupon, inhibited versus uninhibited 5 percent sulfuric acid, indicates that the pyrimidine diones produced by the method of the invention are useful as corrosion inhibitors.

The acid anhydrides produced by the method of the invention, as has been indicated above, can be converted to pyrimidine diones by reaction with an appropriate amine and ring-closure with phosgene. The corresponding sulfur analogues can also be produced by ring-closure with thiophosgene

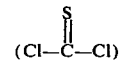

these analogues are preferred as corrosion inhibitors because equilibrium favors the CSH form rather than the favored C=O form of the diones.

1. 4-azaisatoic anhydride having the formula

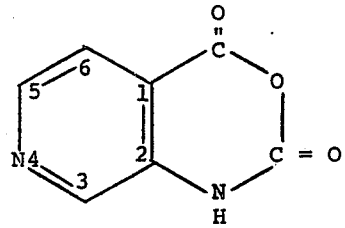

2. 5-azaisatoic anhydride having the formula

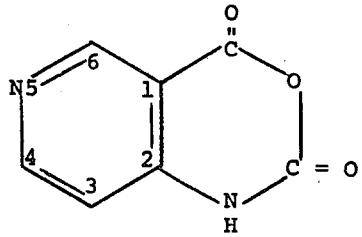

* * * * *